United States Patent
Ogata et al.

(10) Patent No.: US 6,846,949 B2
(45) Date of Patent: *Jan. 25, 2005

(54) FLUORINE-CONTAINING MONOMERIC ESTER COMPOUND FOR BASE RESIN IN PHOTORESIST COMPOSITION

(75) Inventors: Toshiyuki Ogata, Chigasaki (JP); Kotaro Endo, Kanagawa-ken (JP); Hiroshi Komano, Kanagawa-ken (JP)

(73) Assignee: Tokyo Ohka Kogyo Co., Ltd., Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/732,418

(22) Filed: Dec. 11, 2003

(65) Prior Publication Data

US 2004/0122255 A1 Jun. 24, 2004

Related U.S. Application Data

(62) Division of application No. 10/079,506, filed on Feb. 22, 2002, now Pat. No. 6,683,202.

(30) Foreign Application Priority Data

Feb. 22, 2001 (JP) .......................... 2001-47365

(51) Int. Cl.[7] .......................... C07C 69/52; C07C 69/62
(52) U.S. Cl. ........................ 560/220; 560/219
(58) Field of Search ................. 560/219, 220

(56) References Cited

U.S. PATENT DOCUMENTS

| 4,613,657 A | 9/1986 | Narita et al. |
| 6,683,202 B2 * | 1/2004 | Ogata et al. ............... 560/129 |
| 2002/0098440 A1 | 7/2002 | Sato et al. |

FOREIGN PATENT DOCUMENTS

| EP | 0 447 111 | 9/1991 |
| EP | 0 460 941 | 12/1991 |
| JP | 64-43512 | 2/1989 |
| JP | 4-52648 | 2/1992 |
| JP | 9-43848 | 2/1997 |

OTHER PUBLICATIONS

Ogata et al,Proceedings of SPIE–The International Society for Optical Engineering, New Polymer for 157–nm Single–Layer Resist Based on Fluorine Containing Acryl Copolymer, 2001, 4345(Pt. 2, Advances in Resist Technology and Processing XVIII),pp 1048–1055.*

Singh et al., J. Org. Chem., vol. 64, pp. 2873–2876 (1999).

Surya et al., J. Am. Chem. Soc., vol. 111, pp. 393–395 (1989).

Chiba et al., Journal of Photopolymer Science and Technology, vol. 13, No. 4, pp. 647–664 (2000).

* cited by examiner

*Primary Examiner*—Paul A. Zucker
(74) *Attorney, Agent, or Firm*—Wenderoth, Lind & Ponack, L.L.P.

(57) ABSTRACT

The invention discloses a novel ester compound of an unsaturated carboxylic acid represented by the general formula

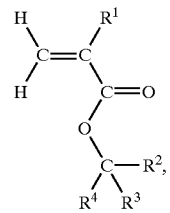

in which $R^1$ is preferably a hydrogen atom or methyl group, $R^2$ is preferably a trifluoromethyl group, $R^3$ is a non-aromatic polycyclic hydrocarbon group or, preferably, an adamantyl group and $R^4$ is preferably a hydrogen atom or methyl group. This unsaturated ester compound is polymerizable to give a (co)polymeric resin which can be used as a base resinous ingredient in a photoresist composition for light exposure with ultraviolet light of a very short wavelength by virtue of the high transparency to the short-wavelength light. A synthetic method for the preparation of the novel ester compound is disclosed.

3 Claims, No Drawings

FLUORINE-CONTAINING MONOMERIC ESTER COMPOUND FOR BASE RESIN IN PHOTORESIST COMPOSITION

This is a divisional of Ser. No. 10/079,506, filed Feb. 22, 2002, now U.S. Pat. No. 6,683,202.

BACKGROUND OF THE INVENTION

The present invention relates to a novel fluorine-containing monomeric ester compound of an unsaturated carboxylic acid. More particularly, the invention relates to a novel fluorine-containing ester compound of acrylic or methacrylic acid as a monomeric compound for the preparation of a polymeric resin suitable as a base resin in photoresist compositions.

Along with the trend in recent years in the technology of semiconductor devices toward a higher and higher degree of integration, LSIs having patterning fineness of the design rule 0.20 μm are already under mass production and a schedule for the industrial production of LSIs of a design rule 0.15 μm is now under programming at a high pace.

While the manufacturing process of semiconductor devices almost always involves fine patterning of a resist layer on a substrate such as silicon wafers by the photolithographic technology utilizing a photoresist composition, the major current for the selection of high-performance photoresist compositions is for the use of a positive- or negative-working chemical-amplification photoresist composition, optionally, in combination with an antireflection coating film to intervene between the photoresist layer and the substrate surface. When an improvement in the photoresist composition or photoresist layer is combined with other improvements including the use of an improved photomask such as a halftone mask and Levenson mask and improvement in the light exposure machines such as the annular illumination, exposure by scanning and use of an optical system of a larger numerical aperture, a patterning fineness of a design rule down to about 0.13 μm is expected to be practically accomplished in the near future.

Needless to say, on the other hand, such fineness of the photolithographic patterning can be accomplished only by the use of an exposure light of an extremely small wavelength. In this regard, the promising short-wavelength light sources to be used in the photolithographic technology of the coming ages or next to the coming ages include ultraviolet lights of 200 nm or shorter wavelength exemplified by the vacuum ultraviolet light (VUV) such as the ArF excimer laser beams of 193 nm wavelength, $F_2$ laser beams of 157 nm wavelength and $Ar_2$ laser beams of 126 nm wavelength and the extreme ultraviolet light (EUV) of 13 nm wavelength.

It is essential in the formulation of a photoresist composition suitable for use in the patterning procedure by the use of the above-mentioned exposure light of an extremely small wavelength that, as in the formulation of photoresist compositions for exposure with KrF excimer laser beams, the base resin ingredient, as the key factor to determine the quality such as pattern resolution and dry etching resistance, is selected from those having high transparency to the exposure light and a structure highly resistant against dry etching.

In this regard, proposals are made in the prior art for the base resin of photoresist compositions including fluorine-containing polymers obtained from a fluorine-containing methacrylate ester monomer by introducing three fluorine atoms as a trifluoromethyl group onto the α-carbon atom of an acrylate ester compound (Japanese Patent Kokai 61-190511, 64-43512, 3-261952, 4-42229 and 4-52648) and a homo- or copolymer of α-trifluoromethyl-1-adamantyl acrylate (Japanese Patent Kokai 9-43848).

When a polymeric resin as desired for a radiation-sensitive resist composition is to be prepared by polymerizing such an acrylate eater monomer having a trifluoromethyl group on the α-carbon atom, however, the monomer cannot be polymerized by the mechanism of radical polymerization but can be polymerized only by the anionic polymerization by the use of n-butyllithioum or pyridine as the catalyst with little versatility relative to the selection of the polymerization procedure. In addition, such a resin has a main chain structure consisting of the monomeric units of the acrylate ester and polycyclic hydrocarbon groups in the pendants so that the transparency of the resin to the exposure light of 200 nm or shorter wavelength cannot be high enough.

With an object to solve this problem, the inventors conducted extensive investigations and previously discovered a promising polymeric resin having a monomeric unit structure derived from an ester of a polycyclic unsaturated hydrocarbon compound represented by the general formula

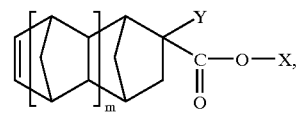

in which X is an acid-dissociable solubility-reducing group, Y is an electron-attracting group and m is 0 or 1.

As compared with the polymeric resin, such as an acrylic polymer, having pendant groups to exhibit improved dry etching resistance, the aforementioned polymeric resin having a main chain structure comprising norbornene rings is excellent in the dry etching resistance but is economically disadvantageous due to the high cost for the synthetic preparation of the monomer compound by a complicated method involving the Diels-Alder reaction from cyclopentadiene or dicyclopentadiene.

SUMMARY OF THE INVENTION

The present invention accordingly has an object to provide, under the above-described situations in the prior art, a novel and inexpensive monomeric compound which can easily be polymerized by a simple and convenient polymerization method to give a radiation-sensitive polymeric resin useful as the base resin in a photoresist composition having high transparency to the photolithographic patterning exposure light and exhibiting excellent resistance against dry etching.

Thus, the novel monomeric compound provided by the present invention is an ester compound of an ethylenically unsaturated carboxylic acid or, in particular, acrylic or methacrylic acid, which ester compound is represented by the general formula

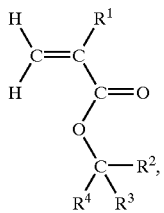

(I)

in which $R^1$ is a hydrogen atom, a fluorine atom, an alkyl group having 1 to 4 carbon atoms or a fluoroalkyl group having 1 to 4 carbon atoms, $R^2$ is a fluorine atom or a fluoroalkyl group having 1 to 4 carbon atoms, $R^3$ is a non-aromatic polycyclic hydrocarbon group and $R^4$ is a hydrogen atom, a fluorine atom, an alkyl group having 1 to 4 carbon atoms or a fluoroalkyl group having 1 to 4 carbon atoms.

In an example for one type of the above-described novel fluorine-containing ester compounds of an unsaturated carboxylic acid, those having a lower alkyl group as $R^4$ can be synthetically prepared by a method comprising the steps of:
(a) reacting a carbonyl compound represented by the general formula $$R^3\text{---CO---}R^4, \qquad (II)$$

in which $R^3$ and $R^4$ each have the same meaning as defined above, with a trialkyl fluoroalkyl silane compound represented by the general formula $$R_3Si\text{---}R^2, \qquad (IIa)$$

in which R is an alkyl group and $R^2$ has the same meaning as defined above, in the presence of a catalyst capable of generating fluorine ions to form an alcohol compound represented by the general formula

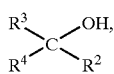

(III)

in which $R^2$, $R^3$ and $R^4$ each have the same meaning as defined above; and
(b) reacting the alcohol compound of the general formula (III) obtained in step (a) above with an acrylic acid or α-substituted acrylic acid represented by the general formula $$CH_2\text{=}CR^1\text{---CO---OH}, \qquad (IV)$$

in which $R^1$ has the same meaning as defined above.

DETAILED DESCRIPTION OF THE PREFERRED EMBODIMENTS

The ester compound of an unsaturated carboxylic acid provided by the present invention as defined by the general formula (I) is a novel compound not described in any prior art literatures. This monomeric compound can readily be polymerized into a polymeric resin which can be used as a base resinous ingredient in a photoresist composition capable of giving a photoresist layer having high transparency to light of a 200 nm or shorter wavelength and exhibiting excellent resistance against dry etching. The high transparency of the polymeric resin obtained by polymerization of such an unsaturated carboxylic acid ester compound can well be understood theoretically by calculation according to the molecular orbital method.

While the above given general formula (I) includes $R^1$ which is a hydrogen atom, a fluorine atom, a lower alkyl group having 1 to 4 carbon atoms or a lower fluoroalkyl group having 1 to 4 carbon atoms, the lower alkyl group is exemplified by methyl, ethyl, propyl and butyl groups but a hydrogen atom and methyl group are preferred as $R^1$ because of the good availability and inexpensiveness of acrylic and methacrylic acids. In addition, the inventive compound of the general formula (I) where $R^1$ is a hydrogen atom or a methyl group has versatility relative to the polymerization method for the preparation of a polymeric resin, which can be selected from a variety of methods including the radical polymerization method, anionic polymerization method, living anionic polymerization method and others, enabling selection of an efficient and inexpensive polymerization method. The fluoroalkyl group as $R^1$ is exemplified by partial fluoroalkyl and perfluoroalkyl groups having 1 to 4 carbon atoms such as a trifluoromethyl group.

It has also been discovered that, when $R^1$ is a fluorine atom or a trifluoromethyl group instead of a hydrogen atom or an alkyl group, the polymer obtained from such an unsaturated ester monomer is imparted with further improved transparency to the $F_2$ laser beams although such a monomeric compound can be polymerized only by the anionic polymerization method with a disadvantage.

The fluorine atom or fluorinated alkyl group having 1 to 4 carbon atoms denoted by $R^2$ in the general formula (I) is a typical electron-attractive group which contributes to the improvement of the polymeric resin obtained from the inventive monomeric ester compound relative to the transparency thereof to ultraviolet lights of 200 nm or shorter wavelength or, in particular, the $F_2$ laser beams. Examples of the fluoroalkyl group as $R^2$ include lower alkyl groups such as methyl, ethyl, propyl and butyl groups substituted by one or more fluorine atoms for a part or all of the hydrogen atoms. Since an increase in the number of substituting fluorine atoms in $R^2$ has an effect of increasing the electron-attractive nature of $R^2$ and hence increasing the transparency of the polymeric resin, perfluoroalkyl groups are preferable as $R^2$, of which trifluoromethyl group is more preferable.

The non-aromatic polycyclic hydrocarbon group as $R^3$ in the general formula (I) has an effect to increase the dry etching resistance of the polymeric resin obtained from the inventive monomeric ester compound. A number of such non-aromatic polycyclic hydrocarbon groups are known in the art, in particular, in the resist composition for ArF excimer laser beam exposure, and the group denoted by $R^3$ can be selected therefrom without particular limitations including norbornyl and adamantyl groups which can be obtained by eliminating a hydrogen atom from a bicycloalkane compound or tricycloalkane compound. An adamantyl group is preferred as $R^3$ in respect of the good availability of the compound used as a starting material in the synthesis of the inventive ester compound.

The $R^4$ in the general formula (I) is, like $R^1$, a hydrogen atom, a fluorine atom, a lower alkyl group having 1 to 4 carbon atoms or a lower fluoroalkyl group having 1 to 4 carbon atoms, which are exemplified by those given above as the examples of the lower (fluoro)alkyl group as $R^1$.

While a large number of the unsaturated ester compounds are encompassed by the definition of the inventive compound represented by the general formula (I), the adamantyl- or norbornyl-substituted compounds expressed by the structural formulas

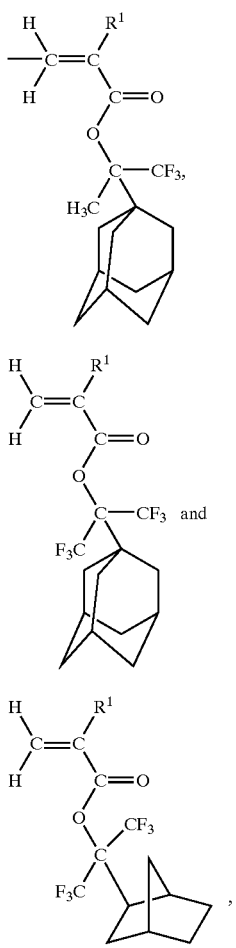

in which $R^1$ has the same meaning as defined before, are the most preferable in respect of the usefulness as a monomeric compound for the preparation of a polymeric resin to be used as the base resin ingredient in photoresist compositions.

Following is a description of the synthetic method for the preparation of the inventive unsaturated ester compound of the general formula (Ia) according to the reaction scheme given below. The starting compound in the first step of the synthetic route is a ketone or aldehyde compound represented by the general formula (II), which is reacted, following the procedure described in Journal of American Chemical Society, volume 111, pages 393–395 (1989) and Journal of Organic Chemistry, volume 64, pages 2873–2876 (1999), with, for example, a trialkyl fluoroalkyl silane compound represented by the general formula $$R_3Si\text{—}R^2, \quad (IIa)$$

in which R is an alkyl group and $R^2$ has the same meaning as defined before, in the presence of a catalyst capable of generating fluorine ions such as cesium fluoride, potassium fluoride and tert-butylammonium fluoride to give an alcohol compound of the general formula (III) having a fluorine atom or fluoroalkyl group as $R^2$ and a non-aromatic polycyclic hydrocarbon group as $R^3$ on the α-carbon atom. This alcohol compound is then reacted with an ester-forming functional derivative of acrylic acid or α-substituted acrylic acid of the general formula $$H_2C\text{=}CR^1\text{—}CO\text{—}X, \quad (V)$$

in which $R^1$ has the same meaning as defined before and X is an ester-forming functional group such as a halogen atom, such as an acid halide to give the inventive unsaturated ester compound of the general formula (I).

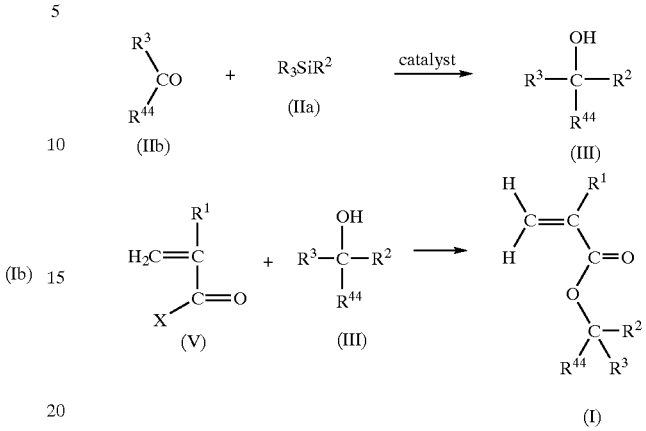

In the above given reaction scheme, $R^{44}$ is a hydrogen atom or a lower alkyl group and the other symbols each have the same meaning as defined before.

On the other hand, in the inventive ester compounds, each of the $R^2$ and $R^4$ is a fluorine atom or a lower fluoroalkyl group and the compounds of the formulas (Ib) and (Ic) can alternatively be synthesized by utilizing the Grignard reaction starting with a Grignard reagent having a non-aromatic polycyclic hydrocarbon group as $R^3$ according to a known procedure described in Journal of Photopolymer Science Technology, volume 13, No. 4, pages 657–664 (2000). The reaction scheme of the Grignard reaction is as follows:

$$R^3\text{—}Mg\text{—}Br+R^2\text{—}CO\text{—}R^4 \rightarrow R^3\text{—}CR^2R^4\text{—}OH,$$

in which each symbol has the same meaning as defined before. The thus obtained alcohol compound is reacted with an ester-forming derivative, e.g., a halide, of an unsaturated carboxylic acid such as acrylic acid which may be substituted by a fluorine atom, lower alkyl group or lower fluoroalkyl group for the hydrogen atom on the α-carbon atom.

The unsaturated ester compound of the general formula (I) obtained in the above-described synthetic route can be polymerized singly or can be copolymerized with one or more of other acrylic monomer compounds to give a polymeric resin usable as a base resinous ingredient in a photoresist composition by dissolving the same in an organic solvent together with an acid-generating agent in the form of a uniform solution. The photoresist composition has sensitivity to ultraviolet light of 200 nm or shorter wavelength such as the $F_2$ laser beams of 157 nm wavelength, ArF excimer laser beams of 193 nm wavelength, $Ar_2$ laser beams of 126 nm wavelength and extreme ultraviolet light of 13 nm wavelength. By virtue of the very specific chemical structure, the inventive ester compound of an unsaturated carboxylic acid is also useful as a monomeric compound having an acid-dissociable solubility-reducing group.

In the following, the present invention is described in more detail by way of an Example, which, however, never limits the scope of the invention in any way.

EXAMPLE

A uniform reaction mixture was prepared by dissolving, in 100 ml of ethyleneglycol dimethyl ether, 8.9 g (0.05 mole) of 1-adamantyl methyl ketone and 7.3 g (0.05 mole) of trimethyl trifluoromethyl silane and, while being kept at a temperature of 0° C., the reaction mixture was admixed with 0.76 g (0.005 mole) of cesium fluoride followed by thorough agitation. After continued agitation of the reaction mixture for 24 hours at room temperature to effect the reaction, the reaction mixture was admixed with 100 ml of a 10 N hydrochloric acid and kept at 60° C. for 12 hours to complete the reaction. The reaction mixture was subjected to extraction with diethyl ether and the extract solution was dried over anhydrous sodium sulfate. The thus dried extract solution was freed from the diethyl ether and then subjected to distillation under reduced pressure to give 10 g of a white solid product which could be identified to be 1-trifluoromethyl-1-(1-adamantyl)ethylalcohol as an intermediate. The yield of this product compound corresponded to 76% of the theoretical value.

The $^1$H-NMR spectral data and the infrared absorption spectral data of this intermediate compound were as follows.

$^1$H-NMR spectral data (δ, ppm, in CDCl$_3$): 1.3 (s, 3H, CH$_3$); 1.65–2.1 (m, 16H).

Infrared absorption spectral data (neat): 3490 cm$^{-1}$ (—OH); 1166–1045 cm$^{-1}$ (—CF).

In the next place, 7.4 g (0.03 mole) of the above obtained intermediate alcohol compound and 3.0 g (0.03 mole) of triethylamine were dissolved in 50 ml of diethyl ether to give a solution which was admixed dropwise with a solution of 3.1 g (0.03 mole) of methacryloyl chloride in 20 ml of diethyl ether under thorough agitation on an ice water bath followed by further continued agitation for 24 hours at 0° C. to effect the esterification reaction. After completion of the reaction, the solution was repeatedly washed three times with 30 ml of a saturated aqueous solution of sodium hydrogen carbonate and then dried over anhydrous sodium sulfate. The thus dried solution was freed from the diethyl ether by distillation and then subjected to distillation under reduced pressure to give 5.0 g of a reaction product which could be identified to be a methacrylic acid ester of 1-trifluoromethyl-1-(1-adamantyl)ethylalcohol. The aforementioned yield of the product compound corresponded to 53% of the theoretical value.

The $^1$H-NMR spectral data and the infrared absorption spectral data of this product compound were as follows.

$^1$H-NMR spectral data (δ, ppm, in CDCl$_3$): 1.3 (s, 3H, CH$_3$); 1.65–2.1 (m, 18H); 5.8 (s, 1H); 6.2 (s, 1H).

Infrared absorption spectral data (neat): 1722 cm$^{-1}$ (—CO—); 1167–1054 cm$^{-1}$ (—CF).

What is claimed is:

1. A fluorine-containing ester compound of an unsaturated carboxylic acid represented by the general formula

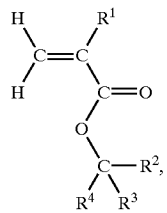

in which R$^1$ is a hydrogen atom, a fluorine atom, an alkyl group having 1 to 4 carbon atoms or a fluoroalkyl group having 1 to 4 carbon atoms, R$^2$ is a fluorine atom or a fluoroalkyl group having 1 to 4 carbon atoms, R$^3$ is a non-aromatic polycyclic hydrocarbon group and R$^4$ is a hydrogen atom, a fluorine atom, an alkyl group having 1 to 4 carbon atoms or a fluoroalkyl group having 1 to 4 carbon atoms.

2. The fluorine-containing ester compound of an unsaturated carboxylic acid as claimed in claim 1 wherein R$^1$ is a hydrogen atom, R$^2$ is a fluoroalkyl group having 1 to 4 carbon atoms, and R$^4$ is a hydrogen atom or an alkyl group having 1 to 4 carbon atoms.

3. The fluorine-containing ester compound of an unsaturated carboxylic acid as claimed in claim 1 wherein R$^1$ is a methyl group, R$^2$ is a fluoroalkyl group having 1 to 4 carbon atoms and R$^4$ is a hydrogen atom or an alkyl group having 1 to 4 carbon atoms.

* * * * *